(12) United States Patent
Johnson et al.

(10) Patent No.: US 7,902,293 B2
(45) Date of Patent: *Mar. 8, 2011

(54) METHOD OF PREPARING EMULSIONS CONTAINING ELASTOMERIC SILANES AND SILOXANES HAVING QUATERNARY AMMONIUM GROUPS

(75) Inventors: Bethany Johnson, Midland, MI (US); Michael Richard Lafore, Freeland, MI (US); Donald Liles, Midland, MI (US); Zuchen Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 1429 days.

This patent is subject to a terminal disclaimer.

(21) Appl. No.: 10/552,204

(22) PCT Filed: Mar. 25, 2004

(86) PCT No.: PCT/US2004/009153
§ 371 (c)(1),
(2), (4) Date: Oct. 6, 2005

(87) PCT Pub. No.: WO2004/104013
PCT Pub. Date: Dec. 2, 2004

(65) Prior Publication Data
US 2006/0193805 A1 Aug. 31, 2006

Related U.S. Application Data

(60) Provisional application No. 60/471,030, filed on May 16, 2003.

(51) Int. Cl.
*C08L 83/00* (2006.01)

(52) U.S. Cl. .......... 524/837; 524/838; 424/70.1; 424/47; 424/59; 424/64; 424/401

(58) Field of Classification Search ....................... None
See application file for complete search history.

(56) References Cited

U.S. PATENT DOCUMENTS

| | | |
|---|---|---|
| 6,475,974 B1 | 11/2002 | LeBoucher |
| 6,482,969 B1 | 11/2002 | Helmrick |
| 6,607,717 B1 | 8/2003 | Johnson |
| 6,787,603 B2 | 9/2004 | Johnson |

FOREIGN PATENT DOCUMENTS

JP  2002-308991  * 10/2010

* cited by examiner

*Primary Examiner* — Jyothsna A Venkat
(74) *Attorney, Agent, or Firm* — Alan Zombeck

(57) ABSTRACT

Oil-in-water (O/W) and water-in-oil (W/O) emulsions and microemulsions containing elastomeric silanes or siloxanes preferably having quaternary ammonium groups are generally made by reacting organic quaternary ammonium compounds having epoxide groups or halohydrin groups, with silanes or siloxanes having amino groups. The reaction is carried out in an aqueous polar phase containing a crosslinking agent and surfactant. The emulsions and microemulsions are especially useful for treating hair, skin, or the underarm.

7 Claims, No Drawings

METHOD OF PREPARING EMULSIONS CONTAINING ELASTOMERIC SILANES AND SILOXANES HAVING QUATERNARY AMMONIUM GROUPS

CROSS REFERENCE TO RELATED APPLICATIONS

This application is a U.S. national stage filing under 35 U.S.C. §371 of PCT Application No. PCT/US2004/009153 filed on Mar. 25, 2004, currently pending, which claims the benefit of U.S. Provisional Patent Application No. 60/471,030 filed May 16, 2003 under 35 U.S.C. §119 (e). PCT Application No. PCT/US2004/009153 and U.S. Provisional Patent Application No. 60/471,030 are hereby incorporated by reference.

This invention is directed to a method of making oil-in-water (O/W) emulsions and microemulsions and water-in-oil (W/O) emulsions and microemulsions containing elastomeric silanes or siloxanes having nitrogen atoms, preferably quaternary ammonium groups, as an oil phase. In particular, the preferred elastomeric silanes or siloxanes are obtained by reacting organic quaternary ammonium compounds having epoxide or halohydrin groups, with silanes or siloxanes having amino groups; and the reaction is carried out in the presence of a crosslinking agent and a surfactant in an aqueous polar phase.

Copending application U.S. Ser. No. 10/306,012, filed Nov. 27, 2002, entitled Method of Making Emulsions Containing Quaternary Ammonium Functional Silanes and Siloxanes (the '012 application); application U.S. Ser. No. 10/001,760, filed Oct. 24, 2001, entitled Silicon Based Quaternary Ammonium Functional Compositions and Methods for Making Them, now U.S. Pat. No. 6,482,969, issued Nov. 19, 2002, (the '969 patent); and copending application U.S. Ser. No. 10/001,753, filed Oct. 24, 2001, entitled Silicon Based Quaternary Ammonium Functional Compositions and Their Applications (the '753 application), are all assigned to the same assignee as the present application, and incorporated herein by reference.

As noted in the '012 application, the '969 patent, and the '753 application, quaternary ammonium functional silanes and quaternary ammonium functional siloxanes have a variety of commercial application in the textile industry and in the personal care arena. They can also be used as anti-microbial agents; in modifying fillers, fibers, and surfaces; as thickening agents; and as a conditioning agent.

In many of these applications and uses, it is often necessary to deliver the quaternary ammonium functional silanes and the quaternary ammonium functional siloxanes as an emulsion or microemulsion. When an emulsion is required, conventional wisdom dictates that the quaternary ammonium functional silane or quaternary ammonium functional siloxane be combined with a surface active agent and water, and mixed until the emulsion is formed.

It is often inconvenient for end users of quaternary ammonium functional silanes and siloxanes to prepare emulsions and microemulsions, and so it would be beneficial to provide a new and simpler process for preparing the emulsions.

While the '753 application describes a method of making emulsions containing quaternary ammonium functional silanes and quaternary ammonium functional siloxanes, the process involves application of conventional wisdom, i.e., the quaternary ammonium functional silane or siloxane is combined with a surface active agent and water, and mixed until an emulsion is formed.

The process according to the present application however, differs significantly from the process used in the '753 application, in that quaternary ammonium functional silanes or siloxanes are actually synthesized in an emulsion, using monomers as starting materials which are reacted together to form the quaternary ammonium functional silane or siloxane, rather than using quaternary ammonium functional silanes or siloxanes. In addition, the quaternary ammonium functional silanes or siloxanes present in the emulsions according to the present invention are elastomers in contrast to fluids which are formed in the emulsion of the '753 application.

This invention relates to methods of making certain oil-in-water (O/W) or water-in-oil (W/O) emulsions and microemulsions containing organosilicon compositions as the oil phase. In particular, these emulsions and microemulsions contain elastomeric silanes or siloxanes, preferably having quaternary ammonium groups in their molecule, as the oil phase. The elastomeric silanes or siloxanes having quaternary ammonium groups are obtained by reacting (i) an organic quaternary ammonium compound having epoxide groups or halohydrin groups in its molecule, with (ii) a silane or siloxane having amino groups in its molecule, in the presence of (iii) a crosslinking agent, (iv) a surfactant, dispersed in (v) an aqueous polar phase.

Representative of suitable quaternary ammonium compounds having epoxide groups and halohydrin groups are glycidyl trimethylammonium chloride, and (3-chloro-2-hydroxypropyl)trimethylammonium chloride, respectively. The aqueous polar phase may be water or a mixture of water and a polar organic compound such as 1,2-hexanediol. These emulsions and microemulsions are useful as treating agents for the hair, skin, and the underarm areas of the human body.

These and other features of the invention will become apparent from a consideration of the detailed description.

DESCRIPTION

As noted above, the invention is directed to oil-in-water (O/W) and water-in-oil (W/O) emulsions and microemulsions containing elastomeric silanes or siloxanes, preferably having quaternary ammonium groups in their molecule, as the oil phase. The elastomeric silanes or siloxanes having quaternary ammonium groups are obtained by reacting (i) an organic quaternary ammonium compound having epoxide groups or halohydrin groups in its molecule, with (ii) a silane or siloxane having amino groups in its molecule. The reaction of components (i) and (ii) is carried out in the presence of (iii) a crosslinking agent, (iv) a surfactant, dispersed in (v) an aqueous polar phase. According to another less preferred process, as illustrated by Example 2, nitrogen containing elastomers can be obtained using only components (ii) to (v), and omitting component (i).

The Silanes & Siloxanes Containing Quaternary Ammonium Groups

These materials are essentially the reaction product obtained by combining components (i) and (ii). A detailed showing of their composition in terms of its structure can be found in detail in the '753 and '760 applications.

Generally, these materials can be described, for purposes herein, as being silanes or siloxanes having in their molecule at least one unit containing a group such as —R—Z-Q bonded to silicon in which:

R is a divalent hydrocarbon group such as ethylene;
Z is a group such as —N(Q1)-; and
Q is a group such as —CH(R)CH(OH)YN$^+$(R$^1$)(R$^2$)(R$^3$)X$^-$;
wherein:
Q1 is a monovalent hydrocarbon group such as methyl;
Y is a divalent hydrocarbon group such as ethylene;
X is a counter ion such as chloride Cl$^-$;
and R$^1$-R$^3$ are monovalent hydrocarbon groups such as methyl.

A representative example therefore of at least one particularly preferred —R—Z-Q group is CH$_2$CH(OH)CH$_2$N$^+$(CH$_3$)$_2$(CH$_3$)Cl$^-$.

The Organic Quaternary Ammonium Compound with Epoxide Groups

Reference may be had to the '753 and '760 applications for a detailed showing of the generic formulas of compounds of this type. Suffice to say, for the purposes herein, some specific examples of useful compounds of this type are glycidyl trimethylammonium chloride and glycidyl trimethylammonium bromide. While non-terminal epoxides may also be used, terminal epoxides such as the compounds described are generally preferred. Combinations of epoxides may also be employed, as well as combinations of epoxides and the halohydrins noted below.

The Organic Quaternary Ammonium Compound with Halohydrin Groups

Again, reference may be had to the '753 and '760 applications for a detailed showing of the generic formulas of compounds of this type. Suffice to say, for the purposes herein, some specific examples of useful compounds of this type are
(3-chloro-2-hydroxypropyl)trimethylammonium chloride ClCH$_2$CH(OH)CH$_2$N(CH$_3$)$_3$Cl,
(3-chloro-2-hydroxypropyl)dimethyldodecylammonium chloride,
(3-chloro-2-hydroxypropyl)dimethyloctadecylammonium chloride,
(3-chloro-2-hydroxypropyl)trimethylammonium bromide,
(3-chloro-2-hydroxypropyl)dimethyldodecylammonium bromide, and
(3-chloro-2-hydroxypropyl)dimethyloctadecylammonium bromide.

While non-terminal halohydrins may also be used, terminal halohydrins such as the compounds described are generally preferred. Combinations of halohydrins may also be employed, as well as combinations of halohydrins and the epoxides noted above.

The Silanes & Siloxane with Amino Groups

Silanes containing amino groups for use herein generally comprise organosilicon monomers of the type R$_3$SiR wherein the R groups in the molecule can consist of alkyl groups containing 1-6 carbon atoms, such as methyl, ethyl, propyl, isopropyl, butyl, and isobutyl; an aryl group such as phenyl; or the R groups can comprise amino groups such as aminoethyl, aminopropyl, aminoisobutyl, aminoethylaminopropyl, and aminoethylaminoisobutyl; provided at least one R group in the silane is an amino group.

Some representative examples of silanes containing amino groups which are suitable for use herein include aminomethyltrimethylsilane, aminotrimethylsilane, (benzylmethylamino)triethylsilane, diethylaminomethyltrimethylsilane, diethylaminotrimethylsilane, diethylaminotriphenylsilane, diisopropylaminotrimethylsilane, dimethylaminotriethylsilane, dimethylaminotrimethylsilane, phenylmethylbis(dimethylamino)silane, tetrakis(dimethylamino)silane, tri-n-hexylsilylamine, trimethylaminosilane, triphenylaminosilane, tris(dimethylamino)ethylsilane, tris(dimethylamino)methylsilane, and tris(dimethylamino)phenylsilane.

Some examples of siloxanes with amino groups include those siloxane polymers and copolymers having number average molecular weights of 1,000-100,000, especially those having number average molecular weight of 5,000-50,000, such as aminopropyl terminated polydimethylsiloxanes and trimethylsilyl terminated dimethylsiloxane copolymers. The siloxanes should also contain 0.1-2.0 milliequivalents of amino functionality per gram of the siloxane on average, based on amino nitrogen of primary and secondary amino groups present in the siloxane. The amino groups may be present in the siloxane as aminoethyl groups, aminopropyl groups, aminoisobutyl groups, aminoethylaminopropyl groups, or aminoethylaminoisobutyl groups. Reference may be had to recently issued U.S. Pat. No. 6,475,974 (Nov. 5, 2002), for details of these and similar siloxanes containing amino groups, which can be used herein.

The Crosslinking Agent

The crosslinking agent for use herein is an organic epoxide containing at least two epoxy groups, i.e., diepoxide, including compositions such as ethylene glycol diglycidyl ether, diethylene glycol diglycidyl ether, polyethylene glycol diglycidyl ether, glycerine diglycidyl ether, triglycidyl ether, propylene glycol diglycidyl ether, butanediol diglycidyl ether; 1,2,3,4-diepoxybutane; 1,2,4,5-diepoxypentane; 1,2,5,6-diepoxyhexane; 1,2,7,8-diepoxyoctane; 1,3-divinylbenzene diepoxide; 1,4-divinylbenzene diepoxide; 4,4'-isopropylidene diphenol diglycidyl ether, and hydroquinone diglycidyl ether.

Other polyglycidyl ethers of alkane polyols, polyglycidyl ethers of poly(allylene glycols), diepoxy alkanes, diepoxy aralkanes, and polyphenol polyglycidyl ethers, can also be used herein.

Two especially preferred organic epoxides containing at least two epoxy groups are shown below, in which n is a positive integer determining the molecular weight of the epoxide.

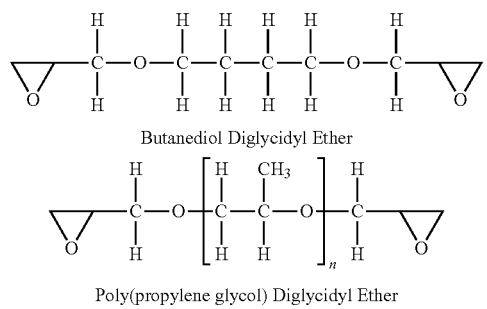

Butanediol Diglycidyl Ether

Poly(propylene glycol) Diglycidyl Ether

When it is desirable to use an epoxy functional silicone containing at least two epoxy groups instead of an organic epoxide containing at least two epoxy groups, a suitable epoxy functional silicone of the general structure shown below can be used, in which x represents an integer of one or more. If desired, epoxy functional silicones can be used which contain pendant epoxy groups along the silicone polymer chain.

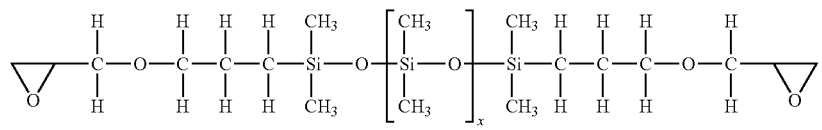

Epoxypropoxypropyl Terminated Polydimethylsiloxane

Such epoxy functional silicones are well known in the art and available commercially from sources such as the Dow Corning Corporation, Midland, Mich. USA. Typically, such silicones have a viscosity ranging from 1 to about 200 centistoke (mm$^2$/s) and weight average molecular weights of about 300-6,000.

Chlorohydrins may be used in place of or in conjunction with the epoxides. As is know in the art, a chlorohydrin is a compound containing both chloro and hydroxyl radicals, and in some cases, chlorohydrin has been defined as compounds having the chloro and the hydroxy groups on adjacent carbon atoms, i.e.,

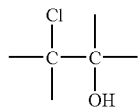

Chlorohydrins can be converted into epoxides by the action of a base. In the presence of the hydroxide ion, a small proportion of the alcohol exists as an alkoxide, which displaces the chloride ion from the adjacent carbon atom to produce a cyclic ether.

In addition, organic epoxides and epoxy functional silicones containing a single epoxy group can also be included as an optional component in order to control the cross link density and the overall molecular weight of the elastomers.

If desired, other types of crosslinking agent can also be employed such as hydroxyalkyl acrylates, some examples of which are hydroxyethyl acrylate and hydroxyethyl methacrylate; as well as isocyanates such as hexamethylene diisocyanate.

The Surfactant

The surfactant may comprise a nonionic surfactant, a cationic surfactant, an anionic surfactant, an amphoteric surfactant, or a mixture of such surfactants. Most preferred however are nonionic surfactants.

Generally, the nonionic surfactant should be a non-silicon atom containing nonionic emulsifier. Most preferred are alcohol ethoxylates $R^4$—$(OCH_2CH_2)_a$OH, particularly fatty alcohol ethoxylates. Fatty alcohol ethoxylates typically contain the characteristic group —$(OCH_2CH_2)_a$OH which is attached to fatty hydrocarbon residue $R^4$ which contains about eight to about twenty carbon atoms, such as lauryl ($C_{12}$), cetyl ($C_{16}$) and stearyl ($C_{18}$). While the value of "a" may range from 1 to about 100, its value is typically in the range of about 12 to about 40.

Some examples of suitable nonionic surfactants are polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether. These and other fatty alcohol ethoxylates are commercially available under trademarks and tradenames such as ALFONIC®, BRIJ, GENAPOL®, NEODOL®, SURFONIC®, TERGITOL®, and TRYCOL. Ethoxylated alkylphenols can also be used, such as ethoxylated octylphenol, sold under the trademark TRITON®.

Cationic surfactants useful in the invention include compounds containing quaternary ammonium hydrophilic moieties in the molecule which are positively charged, such as quaternary ammonium salts represented by R'R"R'"R""N$^+$X$^-$ where R', R", R"', and R"" are alkyl groups containing 1-30 carbon atoms, or alkyl groups derived from tallow, coconut oil, or soy; and X is halogen, i.e., chlorine or bromine. Most preferred are dialkyldimethyl ammonium salts represented by R'R"N$^+$(CH$_3$)$_2$X$^-$, where R' and R" are alkyl groups containing 12-30 carbon atoms, or alkyl groups derived from tallow, coconut oil, or soy; and X is halogen. Monoalkyltrimethyl ammonium salts can also be employed, and are represented by R'N$^+$(CH$_3$)$_3$X$^-$ where R' is an alkyl group containing 12-30 carbon atoms, or an alkyl group derived from tallow, coconut oil, or soy; and X is halogen.

Some representative quaternary ammonium salts are dodecyltrimethyl ammonium bromide (DTAB), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These and other quaternary ammonium salts are commercially available under tradenames such as ADOGEN, ARQUAD, TOMAH, and VARIQUAT.

Among the various types of anionic surfactants which can be used are sulfonic acids and their salt derivatives; alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates such as sodium lauryl (dodecyl) sulfate (SDS); ether sulfates having alkyl groups of eight or more carbon atoms; and alkylaryl sulfonates having one or more alkyl groups of eight or more carbon atoms.

Some examples of commercial anionic surfactants useful in this invention include triethanolamine linear alkyl sulfonate sold under the tradename BIO-SOFT N-300 by the Stepan Company, Northfield, Ill.; sulfates sold under the tradename POLYSTEP by the Stepan Company; and sodium n-hexadecyl diphenyloxide disulfonate sold under the tradename DOWFAX 8390 by The Dow Chemical Company, Midland, Mich.

Amphoteric surfactants which can also be used generally comprise surfactant compositions such as alkyl betaines, alkylamido betaines, and amine oxides, specific examples of which are known in the art.

The Aqueous Polar Phase

The aqueous polar phase used in the process is most preferably an aqueous phase consisting of only water, or an aqueous phase containing water and a polar solvent.

The polar solvents especially preferred herein are those compounds determined to be cosmetically acceptable non-aqueous polar solvents, among which are monohydroxy alcohols such as ethyl alcohol and isopropyl alcohol; diols and triols such as propylene glycol, 1,2-hexanediol $CH_3(CH_2)_3$ $CH(OH)CH_2OH$, 2-methyl-1,3-propane diol $HOCH_2CH$ $(CH_3)CH_2OH$, and glycerol; glycerol esters such as glyceryl triacetate (triacetin), glyceryl tripropionate (tripropionin), and glyceryl tributyrate (tributyrin); and polyglycols such as polyethylene glycols and polypropylene glycols among which are PPG-14 butyl ether $C_4H_9[OCH(CH_3)CH_2]_{14}OH$. In applications other than personal care, these and other non-aqueous polar solvents can be employed.

The aqueous polar phase of the emulsion or microemulsion therefore, can consist of water, or a mixture of water and a polar solvent which is preferably a polar organic compound. Generally, this component will be present in the composition in an amount to provide the balance of the composition to 100 percent, after taking in account the amounts of the other components used in formulating a suitable composition. Typically, however, this component will comprise 0.1-99.8 percent by weight based on the total weight of the O/W or W/O emulsion or microemulsion composition, preferably 10-95 percent by weight. While mixtures of liquids can be used to form this single phase component of the composition, liquids should be miscible and capable of forming an essentially homogeneous mixture.

Optional Components

Since emulsions and microemulsions are susceptible to microbiological contamination, a preservative may be required as an optional component of the composition, and some representative compounds which can be used include formaldehyde, salicylic acid, phenoxyethanol, DMDM hydantoin (1,3-dimethylol-5,5-dimethyl hydantoin), 5-bromo-5-nitro-1,3-dioxane, methyl paraben, propyl paraben, sorbic acid, imidazolidinyl urea sold under the name GERMALL® II by Sutton Laboratories, Chatham, N.J., sodium benzoate, 5-chloro-2-methyl-4-isothiazolin-3-one sold under the name KATHON CG by Rohm & Haas Company, Philadelphia, Pa., and iodopropynl butyl carbamate sold under the name GLYCACIL® L by Lonza Incorporated, Fair Lawn, N.J.

A freeze/thaw stabilizer can be included as another optional component of the composition including compounds such as ethylene glycol, propylene glycol, glycerol, trimethylene glycol, and polyoxyethylene ether alcohols such as RENEX 30 sold by ICI Surfactants, Wilmington, Del.

Another optional component of the composition which can be included is a corrosion inhibitor such as an alkanolamine, an inorganic phosphate such as zinc dithiophosphate, an inorganic phosphonate, an inorganic nitrite such as sodium nitrite, a silicate, a siliconate, an alkyl phosphate amine, a succinic anhydride such as dodecenyl succinic anhydride, an amine succinate, or an alkaline earth sulfonate such as sodium sulfonate or calcium sulfonate.

An additional optional component which can be used are low molecular weight polysiloxanes such as low molecular weight linear or cyclic volatile methyl siloxanes, or low molecular weight linear and cyclic volatile and non-volatile alkyl and aryl siloxanes. Most preferred, are low molecular weight linear and cyclic volatile methyl siloxanes. These compositions are well known in the art and reference may be had to U.S. Pat. No. 6,238,657 (May 29, 2001), for numerous specific examples of suitable compositions.

Alternate Components

When O/W or W/O emulsion or microemulsion compositions according to this invention are used in particular product(s) intended for the personal care market, the compositions may be formulated to include one or more alternate components, for example:

(A) conditioning agents such as cationic polymers, proteins, natural oils, elastomeric silanes and siloxanes containing nitrogen atoms, hydrocarbons other than waxes, and mixtures thereof;

(B) cosurfactants such as betaines, monoalkylalkanolamides, dialkylalkanolamides, amine oxides, amine glycinates, amine propionates, amine sultaines, and mixtures thereof;

(C) polyhydric alcohols such as glycerin and sorbitol.

Products containing alternate components (A) are especially useful as conditioners, products containing (A) and (B) are especially useful as shampoos, and products containing (C) are especially useful as moisturizers.

Preparation

The amount of each of the various components used in preparing emulsions and microemulsions according to the invention, based on the total weight of the composition, is:

(i) 0.01-90 percent by weight of the organic quaternary ammonium compound having epoxide groups or halohydrin groups in its molecule;

(ii) 0.01-90 percent by weight of the silane or the siloxane having amino groups in its molecule;

(iii) 0.01-90 percent by weight of the crosslinking agent;

(iv) 0.01-90 percent by weight of the surfactant, preferably 2-40 percent by weight, more preferably 5-20 percent by weight; and (v) the balance to 100 percent by weight being the aqueous polar phase. Emulsions and microemulsions can also be prepared by omitting component (i), i.e., the organic quaternary ammonium compound having epoxide groups or halohydrin groups in its molecule;

If an optional component is included, it is generally present in an amount of 0.01-0.1 percent by weight of each optional component, i.e., preservative, freeze/thaw stabilizer, or corrosion inhibitor.

The reaction can be made to take place by simply mixing all of the components together, and this is the minimum requirement to obtain reaction, i.e., to perform the "reacting" step under the circumstances. However, it is generally preferred to mix all of the reactants together and to heat them. A catalyst is typically not necessary but under some circumstance, an appropriate catalyst may be employed. In this regard, it has been found that in general, tertiary amines do not add readily to epoxides. This can be improved if the reaction mixture is acidified, especially in stoichiometric proportions, or the tertiary amine is pretreated with an acid in order to convert it to its acid salt.

The emulsions and microemulsions can be prepared using simple propeller mixers, turbine-type mixers, Brookfield counter-rotating mixers, or homogenizing mixers. No special equipment or processing conditions are generally required.

The following examples are set forth in order to illustrate the invention in more detail.

Example 1

Into a reaction vessel was placed 200 gram of a trimethylsiloxy terminated amino functional siloxane having a degree of polymerization (DP) of about 300, and containing about 2 mole percent of aminoethyl aminoisobutyl methyl siloxane groups. 30 gram of Tergitol TMN-6 and 30 gram of Tergitol TMN-10 nonionic surfactants were added, and mixed with a mechanical stirrer for a period of ten to fifteen minutes. 40 gram of water and 0.95 gram of glacial acetic acid were then added to the solution, and allowed to mix for thirty minutes. After mixing, the solution was heated to 75±5° C., and 13.6 gram of glycidyltrimethylammonium chloride was added. This mixture was then stirred for two hours at 75±5° C. Then, 320 gram of water was quickly added to the solution, and mixed rapidly for one hour. An additional 114 gram of water was added, and mixed for thirty minutes. At this time, 15.8 gram of a trimethylsiloxy terminated siloxane having a DP of about 5, and containing three methyl (propyl-3-glycidoxy) siloxane groups, was added to crosslink the amino functional siloxane. This solution was held at 75±5° C. for two hours with stirring. The emulsion was then allowed to cool to room temperature. The final product was a clear emulsion with a visible blue tint containing an elastomeric quaternary ammonium functional siloxane.

Example 2

Into a reaction vessel was placed 200 gram of a trimethylsiloxy terminated amino functional siloxane with a DP of about 300, and containing about 2 mole percent of aminoethyl aminoisobutyl methyl siloxane groups. 30 gram of Tergitol TMN-6 and 30 gram of Tergitol TMN-10 nonionic surfactants were added, and mixed with a mechanical stirrer for a period of ten to fifteen minutes. 40 gram of water and 0.37 gram of glacial acetic acid were then added to the solution, and then it was mixed for thirty minutes. Then, 320 gram of water was quickly added to the solution, and mixed rapidly for one hour. An additional 114 gram of water was added, and mixed for thirty minutes. At this time, 14.6 gram of a trimethylsiloxy terminated siloxane with a DP of about 5, and containing three methyl (propyl-3-glycidoxy) siloxane groups was added to crosslink the amino functional siloxane. This solution was held at 75±5° C. for two hours with stirring. The emulsion was then allowed to cool to room temperature. The final product was a clear emulsion with a visible blue tint containing an elastomeric amine functional siloxane.

Example 2 illustrates another method which can be used, if desired, for making oil-in-water (O/W) and water-in-oil (W/O) emulsions and microemulsions containing elastomeric silanes or siloxanes having nitrogen atoms as the oil phase of the emulsions or microemulsions. It essentially involves the sequential steps of:
(i) preparing a first mixture containing only silanes or siloxanes having amino groups in their molecule and a surfactant;
(ii) preparing a second mixture by adding a first portion of an aqueous polar phase to the first mixture;
(iii) preparing a third mixture by adding the balance of the aqueous polar phase to the second mixture;
(iv) preparing a fourth mixture by adding a crosslinking agent to the third mixture; and
(v) heating the fourth mixture.

Example 3

80 gram of the emulsion of Example 1, i.e., an aqueous emulsion of aminofunctional siloxane partially reacted with glycidyltrimethylammonium chloride, was weighed into a plastic cup. 0.26 gram of 2-hydroxyethylacrylate was added dropwise to the emulsion, the cup was closed, and placed into a Haushild Speedmixer Model TM DAC-150 laboratory mixing device. The contents of the cup were mixed for two cycles of 20 seconds each. The cup was removed from the mixer and allowed to stand undisturbed for four hours, after which 3 gram of the emulsion was poured into a 50 mm plastic Petri dish. The emulsion in the dish was allowed to evaporate at laboratory ambient conditions for 16 hours. An elastomeric film that was insoluble in toluene resulted.

Example 4

80 gram of the emulsion of Example 1, i.e., the aqueous emulsion of aminofunctional siloxane partially reacted with glycidyltrimethylammonium chloride, was weighed into a plastic cup. 0.18 gram of hexamethylenediisocyanate was added dropwise to the emulsion. The cup was closed and placed into a Haushild Speedmixer Model TM DAC-150 laboratory mixing device. The contents of the cup were mixed for two cycles of 20 seconds each. The cup was removed from the mixer and allowed to stand undisturbed for one hour, after which 3 gram of the emulsion was poured into a 50 mm plastic Petri dish. The emulsion in the dish was allowed to evaporate at laboratory ambient conditions for 16 hours. An elastomeric film that was insoluble in toluene resulted.

Example 5

Into a reaction vessel was placed 200 gram of a trimethylsiloxy-terminated amino siloxane having a DP of about 300 and containing about 2 mole percent aminoethyl aminoisobutyl methyl siloxane groups. 30 g of Tergitol TMN-6 and 30 g of Tergitol TMN-10 nonionic surfactants were added, and mixed with a mechanical stirrer for 10-15 minutes. 40 gram of water and 0.37 gram of glacial acetic acid were then added to the solution, and the solution was mixed for thirty minutes. Next, 320 gram of water was quickly added to the solution and the solution was mixed rapidly for one hour. An additional 114 gram of water was added, and the solution was mixed for thirty minutes. 30 gram of the emulsion was weighed into a plastic cup followed by the addition of 0.20 gram of 2-hydroxyethylacrylate. The cup was closed and placed into a Haushild Speedmixer Model TM DAC-150 laboratory mixing device. The contents of the cup were mixed for two cycles of 20 seconds each. The cup was removed from the mixer and allowed to stand undisturbed for one hour, after which 3 gram of the emulsion was poured into a 50 mm plastic Petri dish. The emulsion in the dish was allowed to evaporate at laboratory ambient conditions for 16 hours. An elastomeric film that was insoluble in toluene resulted.

Example 6

30 gram of the aminofunctional emulsion prepared in Example 5 was weighed into a plastic cup followed by the addition of 0.34 gram of hexamethylenediisocyanate. The cup was closed and placed into a Haushild Speedmixer Model TM DAC-150 laboratory mixing device. The contents of the cup were mixed for two cycles of 20 seconds each. The cup was removed from the mixer and allowed to stand undisturbed for one hour, after which 3 gram of the emulsion was poured into a 50 mm plastic Petri dish. The emulsion in the dish was allowed to evaporate at laboratory ambient conditions for 16 hours. An elastomeric film that was insoluble in toluene resulted.

The emulsions and microemulsions prepared herein are useful in personal care, for example, in preparing compositions such as antiperspirants and deodorants. They can be used in skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. They can be used in hair shampoos, hair conditioners, hair colorants, hair relaxers, hair sprays, mousses, permanents, depilatories, and cuticle coats. In cosmetics, the compositions can be added to make-ups, color cosmetics, foundations, blushes, lipsticks, eyeliners, mascara, oil removers, color cosmetic removers, and powders. In such applications, the compositions may include oil soluble, polar solvent soluble, and water soluble ingredients such as vitamins.

The emulsions and microemulsions are also capable of functioning as carriers for pharmaceuticals, biocides, and other biologically active substances; and such compositions have utility as additives for cellulosic or synthetic nonwoven carrier substrates used in wet-like cleansing wipes such as wet-wipes, tissues, and towels, marketed generally for personal hygiene and household cleaning tasks.

Other variations may be made in compounds, compositions, and methods described herein without departing from the essential features of the invention. The embodiments of the invention specifically illustrated herein are exemplary only and not intended as limitations on their scope except as defined in the appended claims.

The invention claimed is:

1. A method of making oil-in-water (O/W) and water-in-oil (W/O) emulsions and microemulsions containing elastomeric silanes or siloxanes having quaternary ammonium groups in their molecule as the oil phase of the emulsion or microemulsion, comprising reacting (i) an organic quaternary ammonium compound having epoxide groups or halohydrin groups in its molecule, with (ii) a silane or siloxane having amino groups in its molecule, in the presence of (iii) a crosslinking agent, and (iv) a surfactant, dispersed in (v) an aqueous polar phase.

2. A method according to claim 1 in which the organic quaternary ammonium compound having epoxide groups is glycidyl trimethylammonium chloride or glycidyl trimethylammonium bromide.

3. A method according to claim 1 in which the organic quaternary ammonium compound having halohydrin groups is selected from the group consisting of
  (3-chloro-2-hydroxypropyl)trimethylammonium chloride,
  (3-chloro-2-hydroxypropyl)dimethyldodecylammonium chloride,
  (3-chloro-2-hydroxypropyl)dimethyloctadecylammonium chloride,
  (3-chloro-2-hydroxypropyl)trimethylammonium bromide,
  (3-chloro-2-hydroxypropyl)dimethyldodecylammonium bromide, and
  (3-chloro-2-hydroxypropyl)dimethyloctadecylammonium bromide.

4. A method according to claim 1 in which the aqueous polar phase consists of water.

5. A method according to claim 1 in which the aqueous polar phase comprises water and a polar organic compound.

6. A method according to claim 5 in which the polar organic compound is selected from the group consisting of monohydroxy alcohols, diols, triols, glycerol esters, and polyglycols.

7. A method according to claim 1 in which the crosslinking agent is selected from the group consisting of organic epoxides containing at least two epoxy groups, epoxy functional silicones containing at least two epoxy groups, chlorohydrins, hydroxyalkyl acrylates, and isocyanates.

* * * * *